United States Patent
Kozokaro et al.

(10) Patent No.: US 11,896,296 B2
(45) Date of Patent: Feb. 13, 2024

(54) END EXPIRIUM IDENTIFICATION METHODS, SYSTEMS, AND PROCESSES

(71) Applicant: Biosense Webster (Israel) Ltd., Yokneam (IL)

(72) Inventors: Kfir Kalman Kozokaro, Haifa (IL); Meir Bar-Tal, Haifa (IL); Shiran Eliyahu, Yokneam Illit (IL); Tal Yehezkel, Pardes Hanna (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 269 days.

(21) Appl. No.: 17/094,302

(22) Filed: Nov. 10, 2020

(65) Prior Publication Data
US 2022/0142705 A1   May 12, 2022

(51) Int. Cl.
*A61B 18/14*   (2006.01)
*A61B 18/00*   (2006.01)

(52) U.S. Cl.
CPC .............. *A61B 18/1492* (2013.01); *A61B 2018/00541* (2013.01); *A61B 2018/00577* (2013.01); *A61B 2018/00773* (2013.01)

(58) Field of Classification Search
CPC ...... A61B 18/1492; A61B 2018/00541; A61B 2018/00577; A61B 2018/00773; A61B 34/25; A61B 34/20; A61B 2034/2051; A61B 90/37; A61B 2017/00243; A61B 5/08
See application file for complete search history.

(56) References Cited

U.S. PATENT DOCUMENTS

| | | | |
|---|---|---|---|
| 5,853,409 A * | 12/1998 | Swanson | A61B 18/00 600/374 |
| 9,414,770 B2 | 8/2016 | Bar-Tal | |
| 10,307,078 B2 | 6/2019 | Bar-Tal | |
| 2012/0172712 A1* | 7/2012 | Bar-Tal | A61B 34/20 600/424 |
| 2012/0197111 A1 | 8/2012 | Bar-Tal | |
| 2013/0243153 A1* | 9/2013 | Sra | A61B 6/485 378/62 |
| 2013/0296845 A1* | 11/2013 | Bar-Tal | A61B 5/6852 606/34 |
| 2016/0235339 A1 | 8/2016 | Bar-Tal | |
| 2016/0262655 A1* | 9/2016 | Bar-Tal | A61B 5/7282 |

OTHER PUBLICATIONS

European Search Report for corresponding EPA No. 21207056.9 dated Apr. 4, 2022.

* cited by examiner

*Primary Examiner* — Khadijeh A Vahdat
*Assistant Examiner* — Marina Delaney Templeton
(74) *Attorney, Agent, or Firm* — Volpe Koenig P.C.

(57) ABSTRACT

The present disclosure provides systems, apparatuses and methods that identify end expirium data based on catheter movement data.

19 Claims, 8 Drawing Sheets

END EXPIRIUM IDENTIFICATION METHODS, SYSTEMS, AND PROCESSES

FIELD OF INVENTION

The present application provides systems, processes, and methods for identifying end expiriums.

BACKGROUND

Surgical procedures involving cavities or chambers, such as the heart, require accurate information regarding a position of a probe or catheter in a cavity. Respiration or breathing causes movement of the catheter while inside a patient, which makes tracking the catheter's position relative to features of the cavity difficult. Respiration is divided into breathing in (inhalation or inspiration) and breathing out (exhalation or expiration). The diaphragm moves up and down during this process and therefore displaces the heart (along with the catheter inside the heart) in a cyclical manner. During the expiration phase, there is a moment called the end-expirium phase, which occurs at the end of the exhalation period, during which displacement from the diaphragm is minimal for a period of time. The normal respiratory cycle is roughly three seconds to eight seconds, but can vary greatly depending on procedure related factors (i.e. medications, pain, anesthesia, ventilation, etc.), and medical conditions (apnea, respiratory diseases, etc.).

Identifying the end expirium is relatively simple over long periods of time. However, it is critical to identify the end expirium in shorter periods of time, particularly for ablation procedures that apply high levels of energy in short time intervals.

SUMMARY

In one aspect, the present disclosure provides systems, apparatuses and methods that identify end expiriums with respect to ablation procedures.

In one aspect, a method is disclosed that includes: (i) identifying an initial end expirium prior to ablation among a plurality of end expiriums; (ii) determining catheter velocity during ablation; and (iii) identifying an estimated end expirium during ablation among the plurality of end expiriums when the catheter velocity is less than a predetermined velocity, and a location of the estimated end expirium is less than a predetermined distance from a location of the initial end expirium.

In another aspect, a system is disclosed that includes a catheter configured to be inserted into a cavity of a patient; at least one sensor configured to detect a position of the catheter; and a processor. The processor is configured to identify an initial end expirium prior to ablation among a plurality of end expiriums; determine catheter velocity during ablation; and identify an estimated end expirium during ablation among the plurality of end expiriums when the catheter velocity is less than a predetermined velocity, and a location of the estimated end expirium is less than a predetermined distance from a location of the initial end expirium.

Multiple different aspects and components of the method and system are described herein.

BRIEF DESCRIPTION OF THE DRAWINGS

A more detailed understanding can be had from the following description, given by way of example in conjunction with the accompanying drawings wherein.

DETAILED DESCRIPTION

As disclosed herein, systems, apparatuses and methods are provided that identify end expirium locations or positions with respect to ablation procedures. One of ordinary skill in the art would understand that the disclosed subject matter could be implemented to identify other features of the respiration cycle. Additionally, one of ordinary skill in the art would understand that the disclosed subject matter could be implemented to be used during procedures other than ablation.

The term probe is used interchangeably with the term catheter herein, and one of ordinary skill in the art would understand that any type of sensing device could be implemented with the configurations disclosed herein.

As used herein, the term end expirium inherently has both a location component and a timing component. In other words, end expirium refers to a specific moment in time with respect to the breathing cycle of a patient. This specific moment in time also has a location component based on a location of the catheter during that moment in time. In specific instances, the term end expirium may be modified herein to refer to the end expirium location, end expirium duration, end expirium position, etc.

Figure 1:
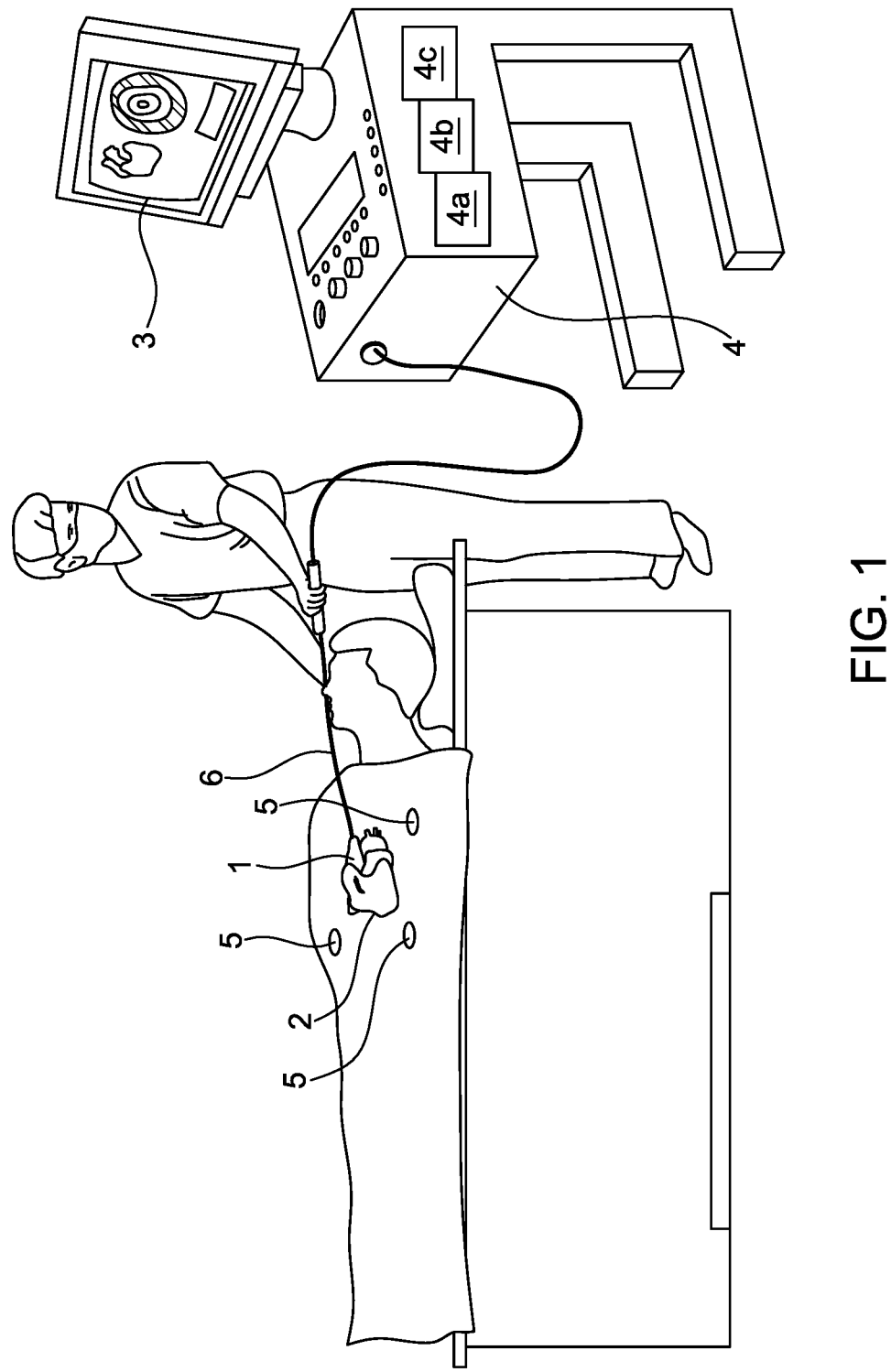
FIG. 1 illustrates an exemplary system according to one embodiment.

FIG. 1 illustrates one embodiment for implementing aspects of the disclosed subject matter. As shown in FIG. 1, a surgeon is navigating a probe or catheter 1 relative to a patient. In one embodiment, the surgeon is navigating a distal tip 6 of the catheter 1 within a patient's heart 2. At least one sensor 5 is attached directly to the patient's body. In one embodiment, the sensor 5 is a patch that is configured to detect magnetic and/or electrical signals. One of ordinary skill in the art would understand based on the present disclosure that the embodiments disclosed herein are not limited to a heart and can be implemented to analyze any type of body part or organ.

On a monitor 3, the surgeon views various data sets and models related to respiration, catheter motion and location, and catheter-heart motion and location. Timestamps for each of these aspects are generated and stored by a computing system 4. The computing system 4 is configured to implement various processes and algorithms disclosed herein. The computing system 4 can include a control unit 4a, a processor 4b, and a memory unit 4c. The control unit 4a can be configured to analyze signals from the catheter 1 and sensors 5 to determine coordinates and positions of the catheter 1 as well as various other information. The memory unit 4c can be of various types, and is generally configured to track position data, respiration data, time data, and other types of data regarding the catheter 1 and the sensors 5. The computing system 4 can be configured to implement any of the steps, processes, methods, configurations, features, etc., that are disclosed herein.

In one aspect, the computing system 4 and/or processor 4b are configured to (i) identify an initial end expirium prior to ablation among a plurality of end expiriums; (ii) determine catheter velocity during ablation; and (iii) identify an estimated end expirium during ablation among the plurality of end expiriums when the catheter velocity is less than a predetermined velocity, and a location of the estimated end expirium is less than a predetermined distance from a location of the initial end expirium.

In one embodiment, the sensor 5 includes at least six sensors formed as patches. In this embodiment, three of the sensors are attached to a patient's chest and three of the sensors are attached to a patient's back. In one aspect, the sensors 5 can be configured to measure inter-impedance among the sensors 5. These sensors 5 assist with modeling a patient's respiratory cycle, and identifying when a patient's lungs are breathing in or out. In one embodiment, when the lungs inflate or fill with air, then the impedance increases. The sensors 5 attached to the patient can also generate a magnetic field, and this magnetic field can be used to detect the absolute position of the catheter 1. One of ordinary skill in the art would understand from the present disclosure that various methods and sensors can be used to determine a patient's respiratory cycle or the catheter's position. The respiration motion gathered from the sensors 5 can be used to generate an ellipsoid that provides a model of the respiration cycle.

When the catheter 1 begins ablating, a generator connected to the catheter 1 that provides a radiofrequency (RF) signal can produce noise, which masks, blocks, or otherwise obfuscates respiration data from the sensors 5. Accordingly, relying solely on this respiration data while using a relatively high energy ablating system makes it difficult to identify the end expirium.

When referring to catheter positions, in one aspect, these positions are filtered using a one second finite impulse response (FIR) filter. One of ordinary skill in the art would understand that various filters and processing can be carried out on the catheter position and velocity signals and data. Catheter velocity can be calculated using the following equation. In Equation 1, position 1 (i.e. $x_1$, $y_1$, $z_1$) and position 2 (i.e. $x_2$, $y_2$, $z_2$) are the catheter positions between two consecutive timestamps TS1 and TS2, respectively.

$$\text{Velocity} = \sqrt{\left(\frac{x_2 - x_1}{TS_2 - TS_1}\right)^2 + \left(\frac{y_2 - y_1}{TS_2 - TS_1}\right)^2 + \left(\frac{z_2 - z_1}{TS_2 - TS_1}\right)^2} \quad \text{(Equation 1)}$$

Figure 5:
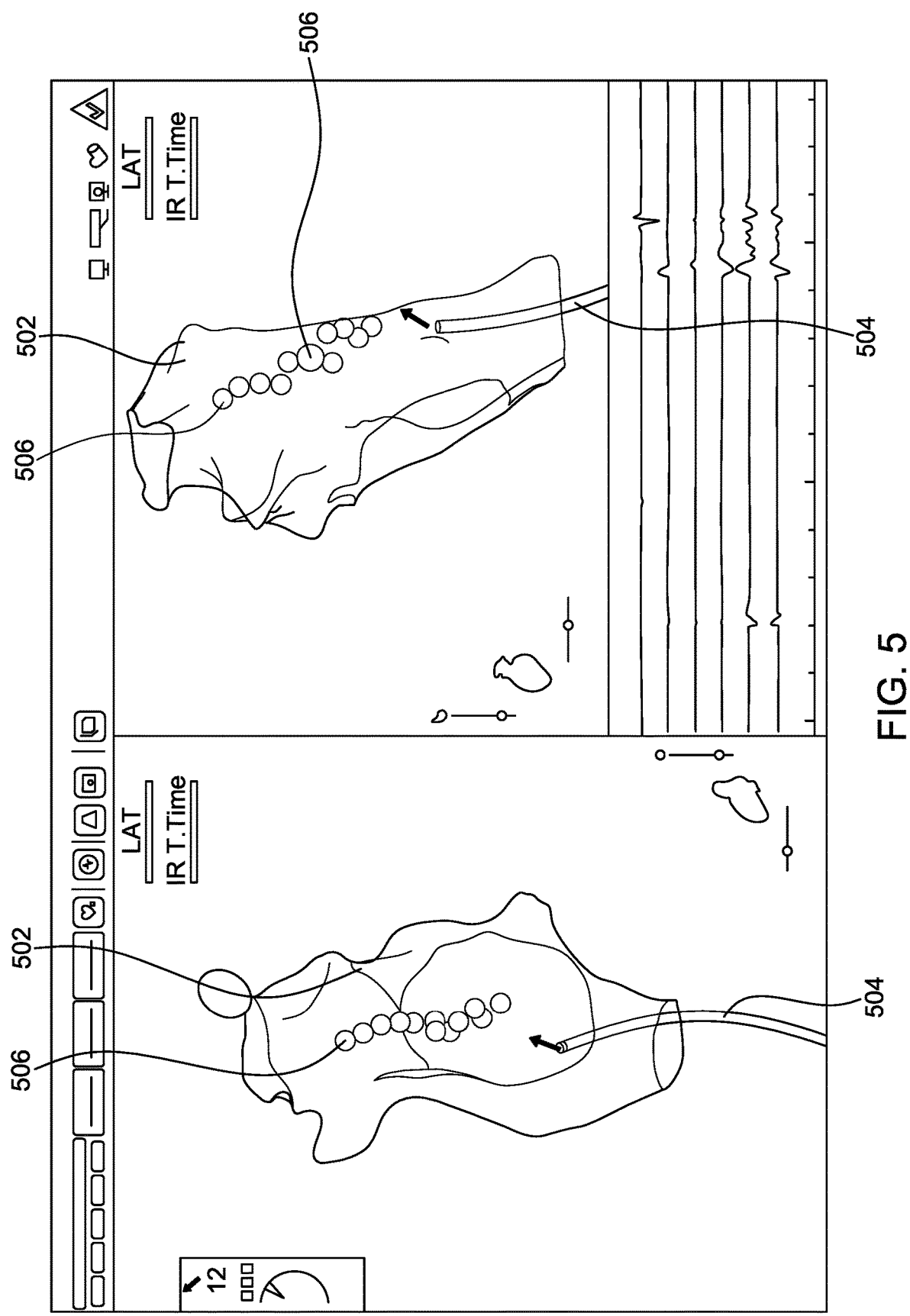
FIG. 5 is an exemplary user interface showing a 3D image of a heart.

As used herein, the term tag, ablation tag, or VISITAG site all generally refer to a notation or marking that is applied to an image (as shown in FIG. 5). More specifically, these terms can refer to a marking or notation on a 3D mapping image of a heart that is automated (based on a processor) to apply an ablation lesion tag. In other words, these indicators are important to indicate to the surgeon where the catheter was located when the ablation was taking place. The tags can include information or data that quantifies the amount of time, contact force, and power that was applied during each ablation session. These tags can be used to help the surgeon understand where ablation has already occurred and helps guide the surgeon to the next potential ablation target site.

FIG. 5 is provided to illustrate one example of the 3D image of a heart 502 that can be used in connection with the disclosed subject matter. As shown in FIG. 5, a catheter 504 is generally shown as being arranged inside of a patient's heart 502. Tags 506 are shown to represent various locations where ablation sessions occurred. A monitor 3, as shown in FIG. 1, is configured to display the image shown in FIG. 5.

In one embodiment, the processes disclosed herein require the following inputs: catheter positions and timestamps; end expirium positions and timestamps; and ablation on/off positions and timestamps. The output of the processes includes site positions in a coordinate system. For example, the output can be provided in the form of X, Y, Z coordinates in a VISITAG module in a CARTO® 3 coordinate system.

Due to certain ablators becoming more powerful, i.e. 90 watts of energy output, the period for ablation has decreased. In certain situations, the ablation period may be as low as four seconds. This development has introduced certain obstacles for determining whether the ablator is stable. First, shorter ablation periods do not necessarily have an end expirium during the ablation. As a result, it may be difficult to tag or locate the ablation sites based on respiration. Second, when applying relatively higher power ablation, respiration measurements experience interference or noise due to the ablation generator. If the respiration data (i.e. respiration indicator data) is unclear or distorted, then it is difficult to identify the end expirium location and timing.

The disclosed subject matter herein is based at least in part on assumptions regarding the end expirium phase. First, the catheter was stable during a previous end expirium. This is based on the fact that expirium is longer than inspirium, and therefore expirium constitutes a majority of the respiration cycle. One of ordinary skill in the art understands that the end expirium phase is relatively short within the expirium phase. Second, the catheter position during a previous end expirium and during ablation is going to be relatively stable. This is based on the physician, surgeon, or doctor, positioning the catheter and maintaining the catheter relatively stable while waiting for the next end expirium. Third, during the end expirium, the catheter velocity is relatively low, and therefore the end expirium phase can be estimated during ablation.

Figure 4:
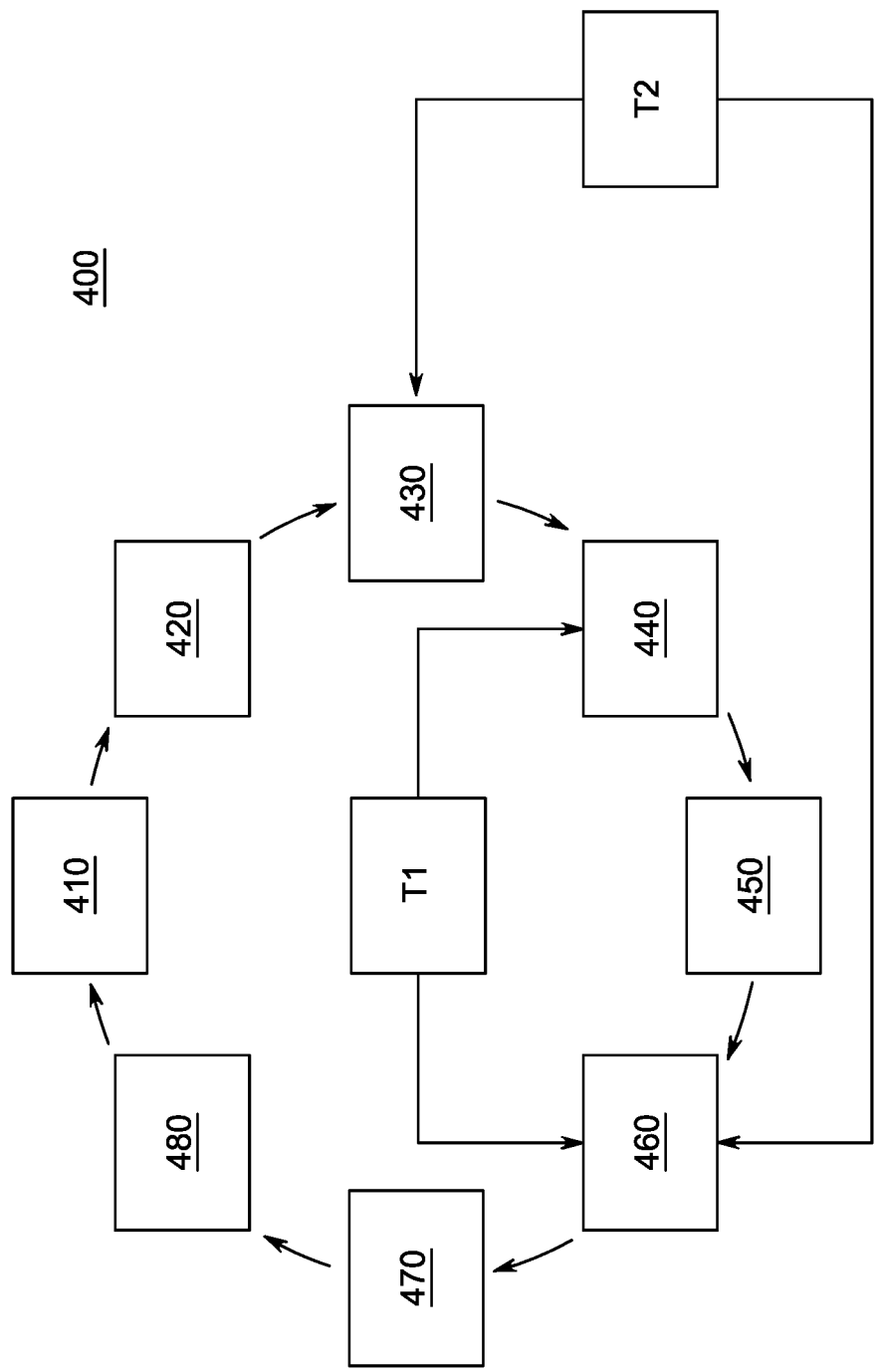
FIG. 4 illustrates a workflow diagram for an ablation session.

FIG. 4 illustrates steps included in an ablation procedure 400. During step 410, a surgeon positions the catheter at a designated ablation site. Step 420 includes the surgeon confirming the location with signal and stability. This involves reviewing the catheter's position and also analyzing the respiration data. Next, at step 430, the surgeon initiates the RF signal for ablation. The RF signal takes a specific period of time to be delivered to the catheter from the generator at step 440. In one instance, this process can take two seconds. This delay or latency is taken into consideration in step 245 of FIG. 2, which is explained in more detail below. After the RF signal is delivered, then the surgeon confirms stability of the catheter during the ablation at step 450. Finally, an ablation tag is formed at the end of the ablation period at step 460.

Between the RF signal being delivered (step 440) and the ablation tag being formed (step 460), a time interval T1 can pass. In one aspect, time interval T1 is four seconds. Between the surgeon initiating the RF signal at step 430 and the ablation tag being formed at step 460, a time interval T2 can pass. In other words, the ablation session generally lasts up to six seconds, which includes pre-ablation time of two seconds and RF session of four seconds. The two second delay is based on the RF generator pump flow rate being required to be set at a high flow rate for at least two seconds prior to starting the actual ablation.

After the ablation tag is formed, the surgeon can then confirm different metrics regarding the ablation (step 470) and move to the next site targeted for ablation (step 480). The ablation tag from the previous site assists and helps the surgeon navigate to the next site.

The present embodiments address the issues identified above by identifying end expirium based on catheter movement. When tracking the catheter's movement, the end expirium is typically located in an area of the curve representing the catheter's position when catheter velocity is the slowest. This assumption is verified by comparing a current end expirium location to a previous end expirium location (i.e. before ablation), and checking for a distance between these two locations against a predetermined threshold. The present embodiments disclose systems, methods, and algorithms to carry out this process. In other words, the present disclosure identifies a process for identifying the end expirium phase without relying on the sensors (i.e. chest sensors and back sensors) attached to a patient's body. In one aspect, the embodiments disclosed herein focus on the time period immediately before respiration to identify a critical time when there is the least amount of motion from the diaphragm imparted onto the heart.

Figure 2:
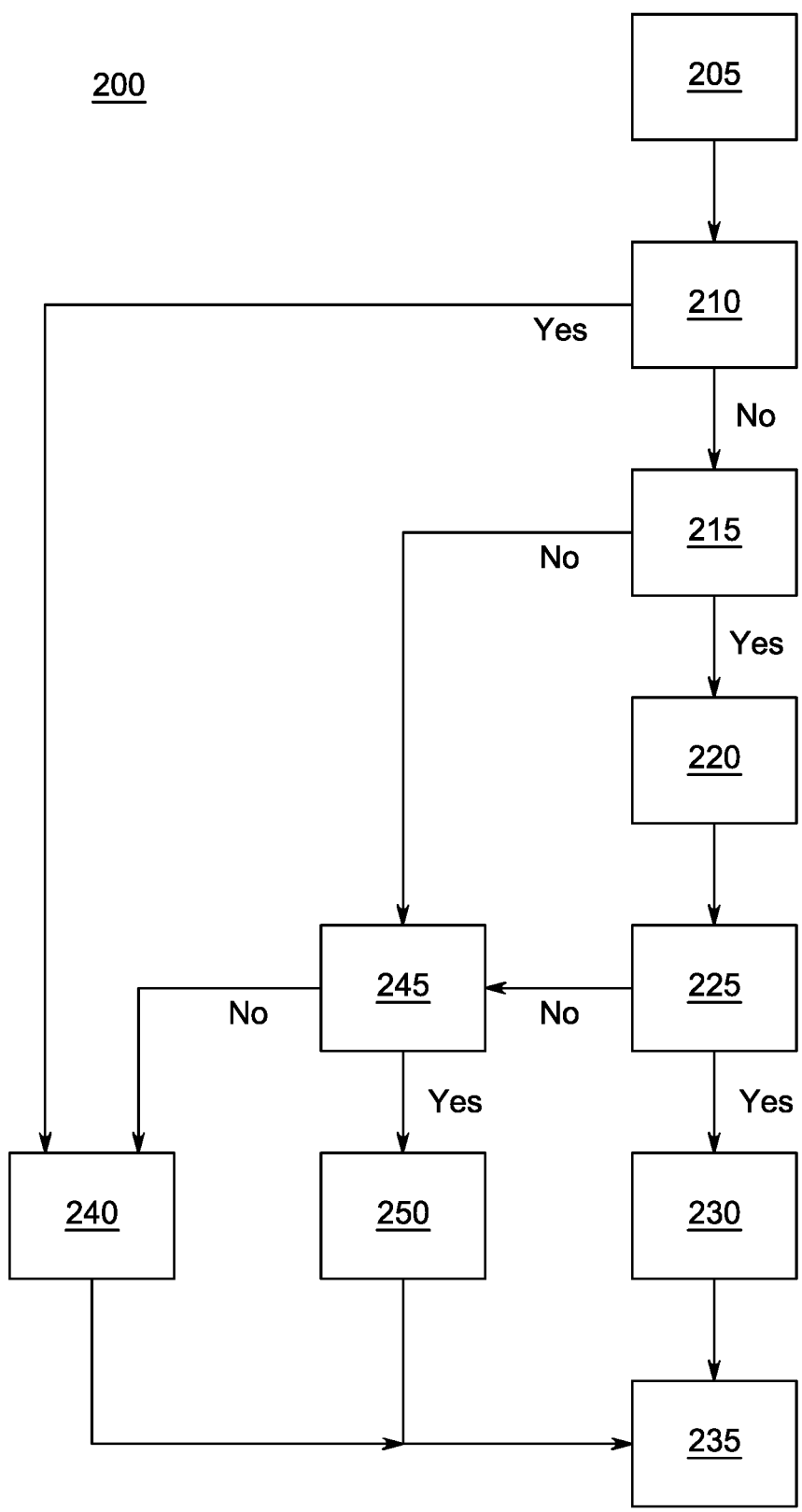
FIG. 2 illustrates a flow diagram including steps according to one embodiment of a process.

FIG. 2 illustrates a flow diagram detailing steps in a process 200 for identifying the end expirium. The process starts at step 205, which can include the surgeon positioning a catheter within a patient's heart. Next, step 210 includes identifying an initial end expirium among a plurality of end expiriums prior to ablation. The term initial end expirium is used synonymously with the last or prior end expirium. End expirium timestamps can be generated during navigation of the catheter before, during, and after ablation. The process inherently includes saving all previous end expirium data detected by the system. The initial end expirium is detected by using respiration information or sensors in one aspect. For example, the sensors 5 or electrodes on the probe 1 can provide this information.

Step 210 also includes a validation step in which it is determined whether the initial end expirium was recorded during an ablation procedure.

In the event that the end expirium data is recorded during ablation at step 210, then step 240 occurs. Step 240 includes setting an ablation tag or site at a first or initial position of the catheter when ablation began. The position of the catheter in this situation corresponds to approximately two seconds after the RF signal was first triggered, i.e. when the RF signal is actually delivered.

If an end expirium did not occur during ablation, then the process proceeds to step 215 in which there is a comparison of the catheter velocity relative to a predetermined threshold. In one embodiment, the predetermined threshold is 5 mm/second. If the catheter velocity is above the predetermined threshold (i.e. the catheter velocity is too fast), then the process proceeds to step 245. One of ordinary skill in the art would understand based on the present disclosure that the predetermined threshold velocity can vary.

If the catheter velocity is below the predetermined threshold (i.e. the catheter is relatively stable), then the process proceeds to step 220. In step 220, the process identifies or find the closest location to the initial end expirium (i.e. the last end expirium) prior to ablation. This closest location corresponds to an estimated end expirium.

Proceeding from step 220, the next step 225 evaluates whether a distance from the estimated end expirium is less than a predetermined distance from the initial end expirium. In one embodiment, the predetermined distance is 3 mm. This relatively small distance ensures that the estimated end expirium and the initial end expirium are close enough to each other. One of ordinary skill in the art would understand based on the present disclosure that the predetermined threshold distance can vary.

If the distance from the estimated end expirium is less than the predetermined distance from the initial end expirium, then the process proceeds to step 230 in which an ablation tag or site is set at the estimated end expirium, which corresponds to a location of the catheter during relatively low velocity (i.e. below the velocity threshold) that is closest to the initial end expirium. Step 235 ends the process 200.

If the distance from the estimated end expirium is greater than the predetermined distance from the initial end expirium, then the process proceeds to step 245. Step 245, which can be invoked or triggered by negative responses from step 215 (i.e. checking catheter velocity versus a threshold velocity) or step 225 (i.e. checking end expirium distance relative to a threshold distance), checks whether the initial end expirium is two seconds or less prior to starting ablation. If yes, then step 250 occurs, which includes setting an ablation tag at the initial end expirium location. If no, then step 240 occurs.

In summary, at the end of process 200, an ablation site or tag is set at one of the three following positions: the initial end expirium location; catheter location closest to the initial end expirium; or a first or initial position of the catheter when ablation was initiated. The process 200 does not rely on respiration indicators to identify the estimated end expirium, and is independent of any information generated by sensors attached to the patient regarding respiration (i.e. electrical current or impedance signals generated by respiration). In other words, the process (as well as the processor implementing this process or system associated with the process) is configured to identify the end expirium solely based on catheter movement data.

In one aspect, the present disclosure essentially identifies the time and position of the catheter when catheter velocity is the slowest. The process then identifies the longest of these relatively slow catheter velocity periods. This information is then compared against the previous or last end expirium. In other words, since there is not enough time due to the shortened ablation period to analyze a full respiration cycle during ablation, the process disclosed herein uses the position of the previous end expirium and uses this to extrapolate or identify the next end expirium (i.e. the end expirium during ablation). By comparing these two end expirium locations, it can be determined whether the catheter was stable during ablation if the distance between the two location is below a predetermined threshold (i.e. 3 mm).

In one aspect, the process can include the following steps. A central processor, module, or CPU (generically referred to as a processor in the following context) stores or saves any last end expirium (i.e. previous end expirium or initial end expirium) that was detected by the system. When ablation is detected, then the processor is collecting catheter position data. In situations where the last end expirium occurred during ablation, then the processor sets a tag (i.e. a VISITAG Site) at the first position of the catheter during ablation. The catheter velocity is calculated by the processor using the catheter positions, and specifically focuses on the catheter stable positions. Catheter positions or timestamps that have a velocity greater than 5 mm per second are excluded from the data results. In other words, only catheter positions or timestamps having a relatively lower velocity are considered for potential ablation tag sites. The distance between the catheter position of the end expirium prior to ablation and the catheter positions having a velocity less than 5 mm per second are then calculated and compiled. A low velocity position having the smallest or minimal distance to the catheter position during the prior or last end expirium is then selected as a potential candidate location for the ablation tag or site. If the distance is between the prior end expirium and the current location is less than 3 mm, then the candidate location is confirmed for an ablation tag. In other words, the VISITAG Site is set at this position. If the previous end expirium before ablation occurred within two seconds from the start of the ablation, then the ablation tag is set at the catheter position during the previous end expirium. If (1) the distance between the candidate location and the previous end expirium is 3 mm or greater, or (2) the catheter velocity was above 5 mm per second and the previous end expirium was within two seconds of the ablation, then the ablation tag is set to a first catheter position during ablation. This position corresponds to when the RF signal is delivered and ablation actually starts, which can be around two seconds after the RF signal is triggered.

The features of the present disclosure were validated for accuracy and reliability. In one aspect, the movement of a catheter was analyzed to identify purely respiration-based movement and purely catheter movement. Using this information, the end expirium was then identified using known methods that rely on respiration data. This information was then compared to data generated using features according to the present disclosure. The data generated using the features according to the present disclosure essentially matched (within an acceptable range of variation) the end expirium information generated according to other methods. In one aspect, the comparison between the two sets of data and information produced a +/−3 mm range difference in the end expirium locations. The results are described in more detail herein.

Figure 3:
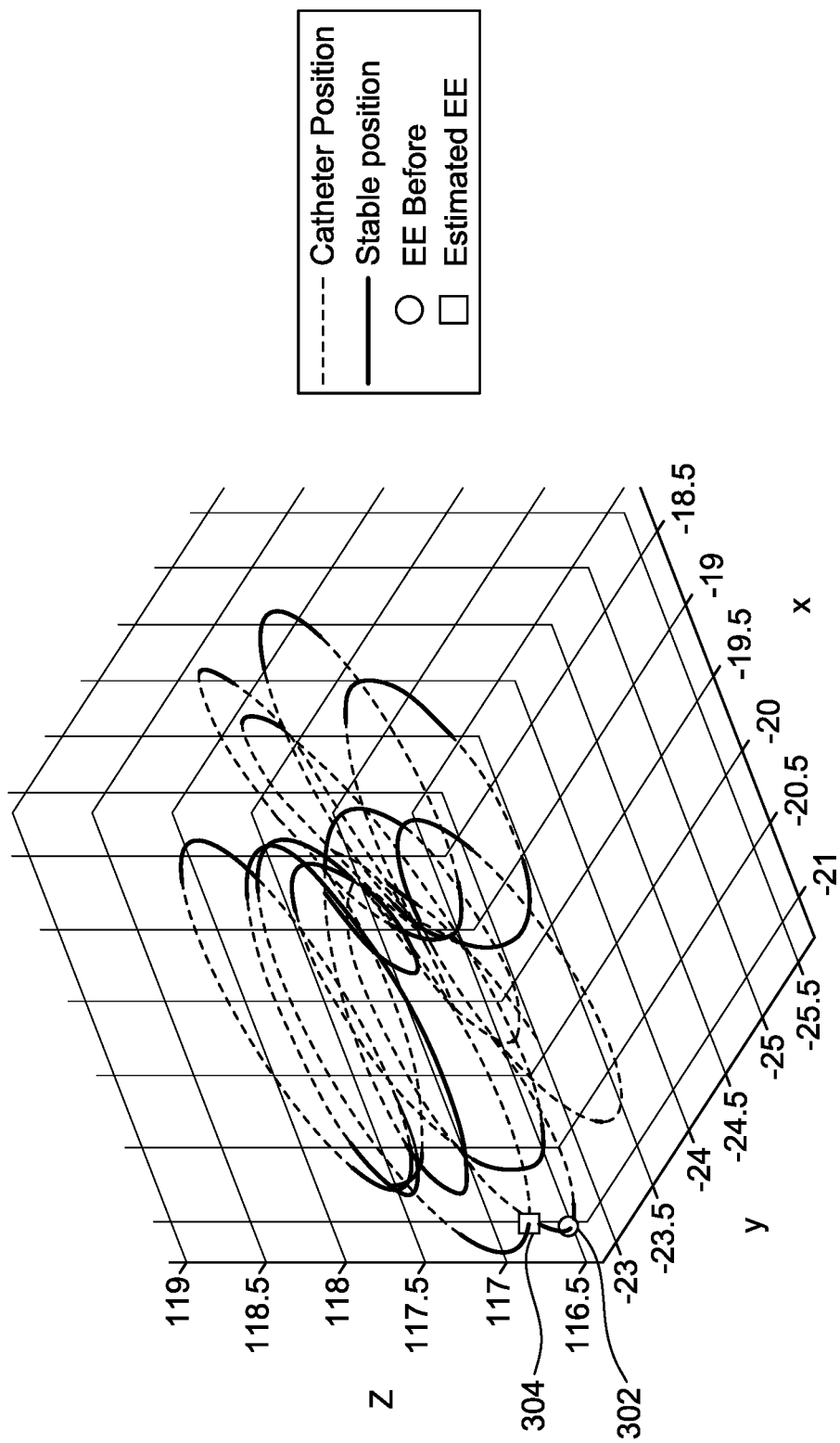
FIG. 3 illustrates a catheter position graph.

FIG. 3 is a 3D motion graph that tracks the catheter position. The catheter position is generally shown in a repeating ellipse pattern due to respiration movement. A stable position of the catheter is also indicated on the graph. As shown in the graph, the stable positions generally are at the end curves of the ellipse. This is based on the expirium and inspirium phases of respiration. The last end expirium 302 before ablation and the estimated end expirium 304 (as calculated based on the processes disclosed herein) are shown in FIG. 3. As shown in FIG. 3, a distance of mm is defined between end expirium 302 and estimated end expirium 304. This distance reinforces that the last end expirium before ablation can reliably be used as an estimated end expirium, under certain conditions as explained in this disclosure.

Figure 6:
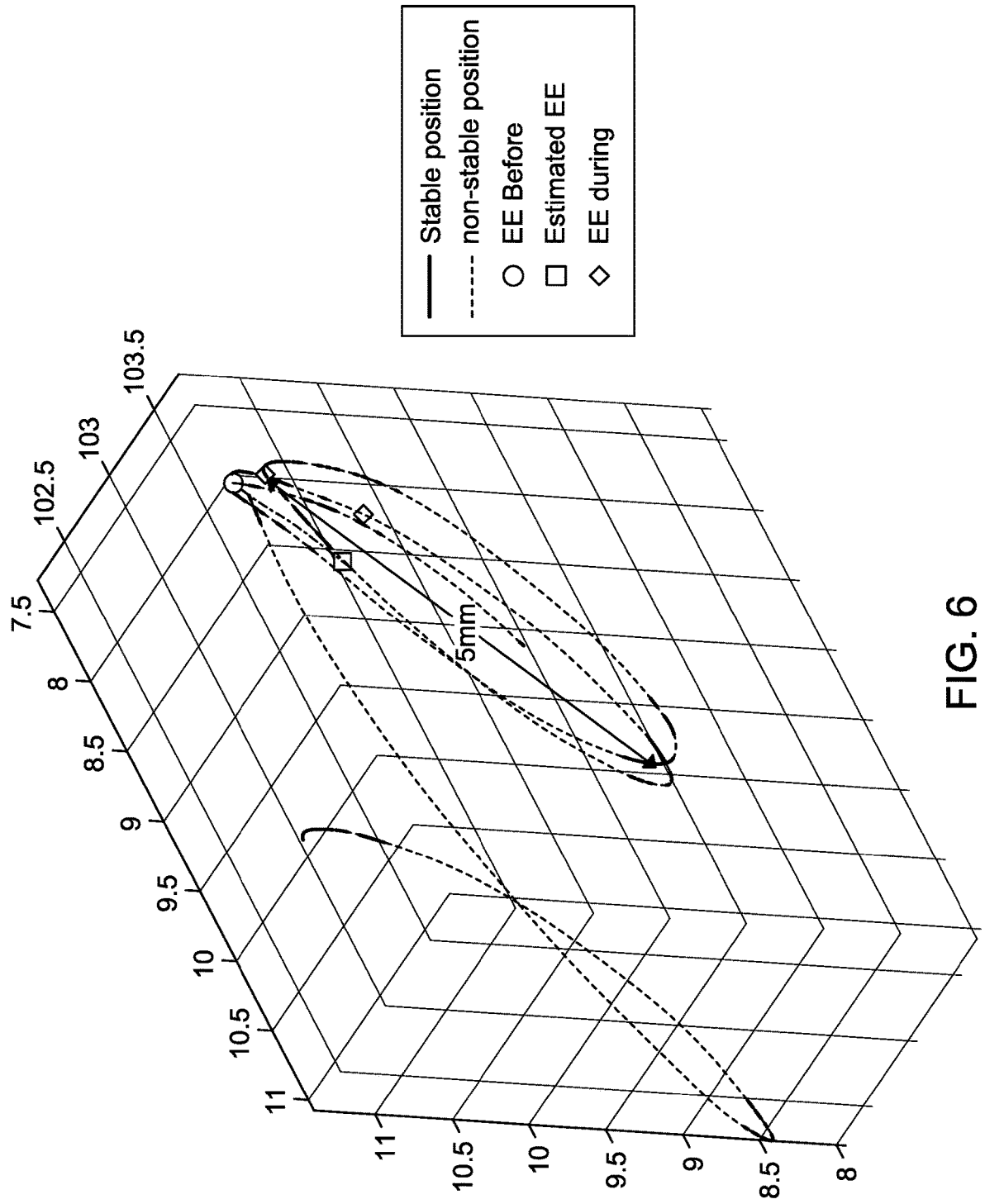
FIG. 6 illustrates a comparison between end expiriums based on catheter position.
Figure 7A:
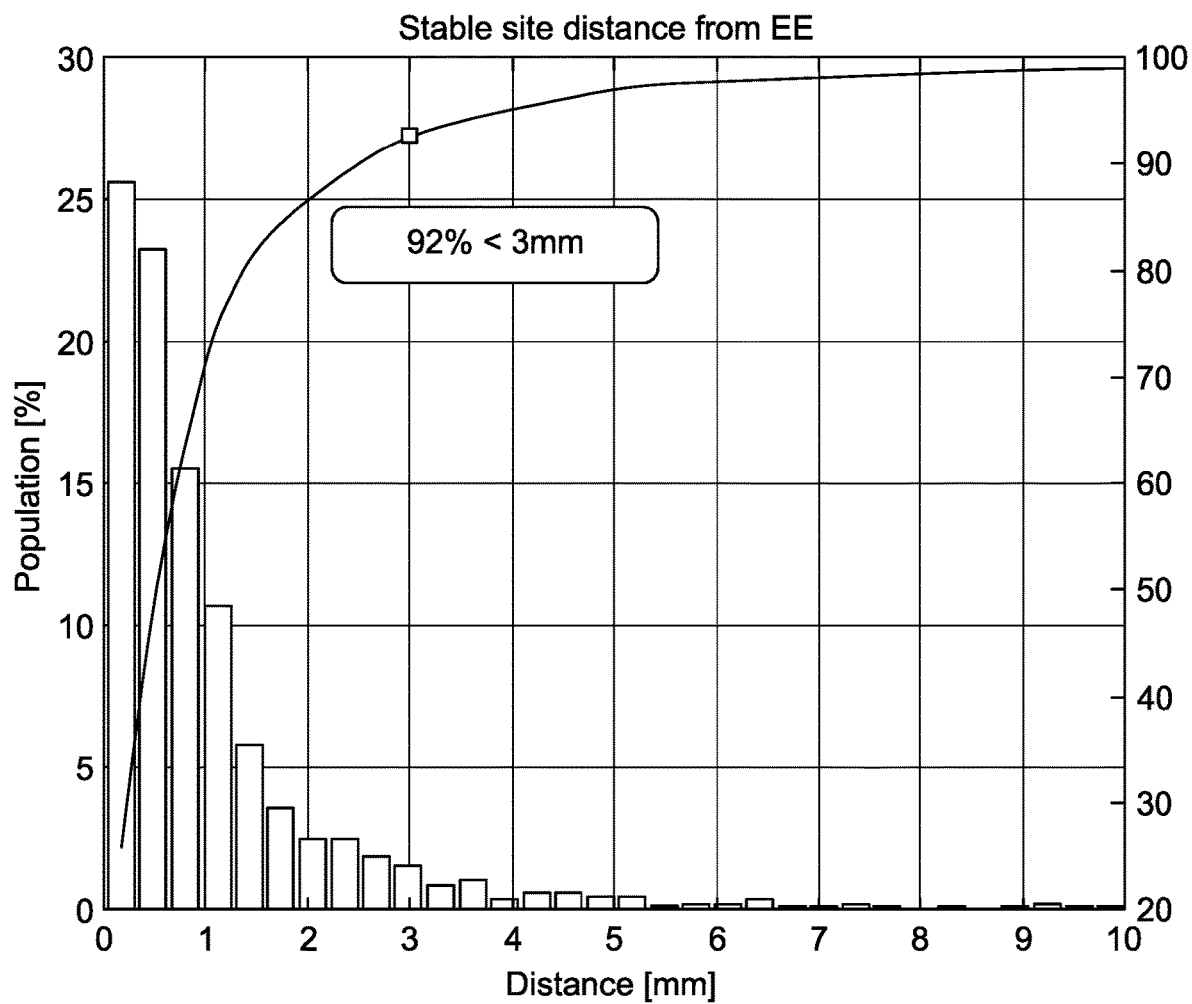
FIG. 7A illustrates site stability data with respect to a validation process for conscious patients.
Figure 7B:
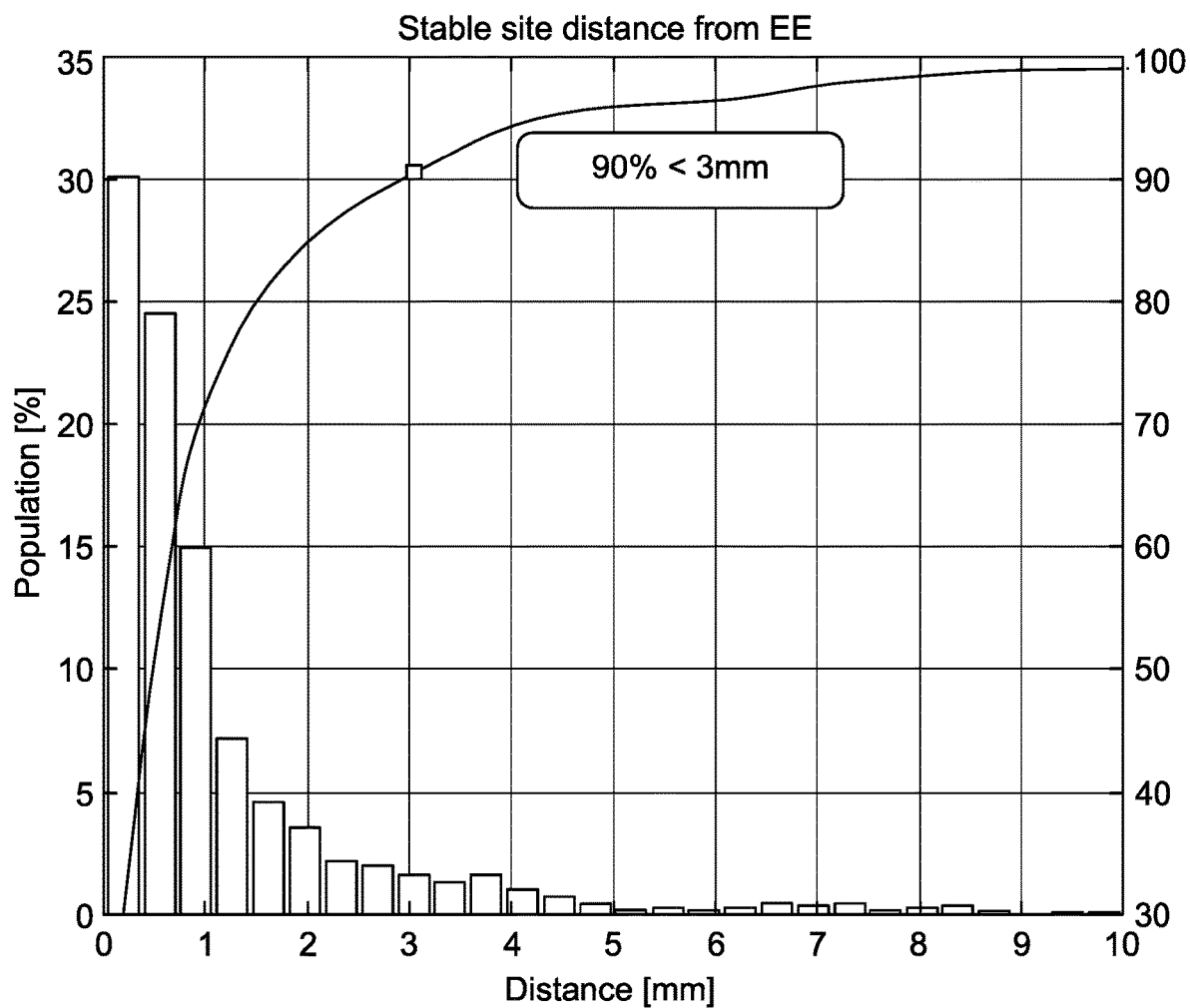
FIG. 7B illustrates site stability data with respect to a validation process for anesthetized patients.

As shown in FIGS. 6, 7A, and 7B, the disclosed subject matter has been validated. In FIG. 6, validation was performed to illustrate that the relatively small distance between an end expirium location before ablation to the closest low velocity position during ablation (i.e. the estimated end expirium).

As shown in FIG. 7A, for conscious patients, the results of using the disclosed subject matter resulted in 92% of the estimated end expirium locations being within 3 mm of the last end expirium prior to ablation. FIG. 7B illustrates a 90% correspondence rate of the estimated end expirium location being within 3 mm of the last end expirium prior to ablation for sedated patients. Outliers or situations where the estimated end expirium did not correlate to the last end expirium within the predetermined thresholds were generally limited to situations in which the catheter was not stable during ablation, the catheter was repositioned form the last end expirium before ablation to a different location, or the ablation period was less than three seconds (which is typically caused by a surgeon intentionally aborting the ablation session).

In one aspect, the disclosed subject matter relies on the catheter being relatively stable during ablation. While respiration motion will inherently move the catheter (along with the heart), it is generally assumed that the surgeon maintains the catheter in a relatively stable position during ablation in order to ensure that catheter ablates a specific portion of the heart. In one aspect, it is also important for the catheter to remain generally close to its position during the initial or prior end expirium.

The disclosed subject matter has been validated in a wide range of subjects and situations. The disclosed subject matter provides reliable end expirium data in patients that are ventilated (under anesthesia) and non-ventilated (conscious but under sedation).

The subject matter disclosed herein can be implemented using any one or more of the following Biosense Webster, Inc. components or interfaces: CARTO® 3 System Qmode+ Software, Qdot Catheter, nMARQ™ RF Generator and Coolfow Pump, VISITAG® module, and Pentaray Nav Catheter. One of ordinary skill in the art would understand that the disclosed subject matter could be implemented with various other components and interfaces.

The disclosed subject matter provides a solution for avoiding the issues associated with distorted or noise-laden respiration signals that occur during high power ablation procedures. The Applicant recognized that there was a need to identify end expiriums during relatively high-powered ablation procedures without relying on respiration indicator information. This is achieved in one aspect by relying on the catheter position instead of the respiration indicators during ablation to identify the end expirium. In other words, an estimated end expirium is identified independent from respiration indicators.

The disclosed subject matter is not limited to being used in connection with a heart. The disclosed subject matter can be used in a variety of applications to analyze features of any type of object, such as a chamber.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A method of identifying an end expirium, the method comprising:
   (i) identifying an initial end expirium prior to ablation, the initial end expirium associated with a first catheter position;
   (ii) determining catheter velocity and catheter position during ablation; and
   (iii) identifying an estimated end expirium during ablation among a plurality of end expiriums when the catheter velocity is less than a predetermined velocity, and when the catheter position is less than a predetermined distance from the first catheter position;
   wherein the estimated end expirium is identified among the plurality of end expiriums based on the estimated end expirium having a lowest catheter velocity for a longest period of time among the plurality of end expiriums.

2. The method of claim 1, wherein the predetermined velocity is 5 mm/second.

3. The method of claim 1, wherein the predetermined distance is 3 mm.

4. The method of claim 1, further comprising setting an ablation tag at the estimated end expirium.

5. The method of claim 1, further comprising:
   determining a period between the initial end expirium and ablation when the catheter velocity is greater than the predetermined velocity.

6. The method of claim 1, wherein the ablation uses radiofrequency signals having an output power of 90 watts.

7. The method of claim 1, wherein the estimated end expirium is identified independent from respiration indicators.

8. A method, comprising:
   (i) identifying an initial end expirium prior to ablation;
   (ii) monitoring a catheter velocity from a first time corresponding to the initial end expirium to a second time corresponding to ablation;
   (iii) identifying a period between the first time and the second time during which the catheter velocity is greater than a velocity threshold; and
   (iv) setting an ablation tag at a position of the catheter during ablation, responsive to the identified period being greater than a duration threshold.

9. A method, comprising:
   (i) identifying an initial end expirium prior to ablation;
   (ii) monitoring a catheter velocity from a first time corresponding to the initial end expirium to a second time corresponding to ablation;
   (iii) identifying a period between the first time and the second time during which the catheter velocity is greater than a velocity threshold; and
   (iv) setting an ablation tag at the first time, responsive to the identified period being less than a duration threshold.

10. A system for identifying an end expirium, the system comprising:
    a catheter configured to be inserted into a cavity of a patient;
    at least one sensor configured to detect a position of the catheter; and
    a processor configured to identify an estimated end expirium during ablation among a plurality of end expiriums based on the estimated end expirium having a lowest catheter velocity for a longest period of time among the plurality of end expiriums.

11. The system of claim 10, wherein the predetermined velocity is 5 mm/second.

12. The system of claim 10, wherein the predetermined distance is 3 mm.

13. The system of claim 10, wherein the at least one sensor is configured to detect respiration indicators, and the processor is configured to identify the estimated end expirium without relying on the respiration indicators.

14. The system of claim 10, wherein the processor is further configured to provide an ablation tag at the estimated end expirium.

15. The system of claim 10, wherein the processor is further configured to determine a period between the initial end expirium and ablation when the catheter velocity is greater than the predetermined velocity, and set an ablation tag at a first position during ablation when the period is greater than a predetermined length.

16. The system of claim 10, wherein the processor is further configured to determine a period between the initial end expirium and ablation during which the catheter velocity is greater than the predetermined velocity, and is configured to set an ablation tag at the initial end expirium when the period is less than a predetermined length.

17. The system of claim 10, wherein the catheter is configured to ablate using radiofrequency signals having an output power of 90 watts.

18. The system of claim 10, wherein the processor is configured to identify the estimated end expirium when a velocity of the catheter is less than a predetermined velocity, and the position of the catheter is less than a predetermined distance from a first position of the catheter during an initial end expirium prior to ablation.

19. The system of claim 10, wherein the processor is configured to identify the end expirium solely based on catheter movement data.

* * * * *

UNITED STATES PATENT AND TRADEMARK OFFICE
CERTIFICATE OF CORRECTION

| | | |
|---|---|---|
| PATENT NO. | : 11,896,296 B2 | Page 1 of 1 |
| APPLICATION NO. | : 17/094302 | |
| DATED | : February 13, 2024 | |
| INVENTOR(S) | : Kozokaro et al. | |

It is certified that error appears in the above-identified patent and that said Letters Patent is hereby corrected as shown below:

On the Title Page

In Item (74), under "Attorney, Agent, or Firm", in Column 2, Line 1, delete "Volpe Koenig P.C." and insert -- Volpe Koenig --, therefor.

In the Specification

In Column 3, Line 32, delete "radiofrequency" and insert -- radio frequency --, therefor.

In Column 3, Line 65, delete "guide" and insert -- to guide --, therefor.

In Column 7, Line 1, delete "velocity less" and insert -- velocity of less --, therefor.

In Column 7, Line 6, delete "distance is" and insert -- distance --, therefor.

In Column 7, Line 53, delete "that the" and insert -- the --, therefor.

In Column 7, Line 67, delete "form" and insert -- from --, therefor.

In Column 8, Line 36, delete "independent" and insert -- independently --, therefor.

In the Claims

In Column 9, Line 42, in Claim 6, delete "radiofrequency" and insert -- radio frequency --, therefor.

In Column 9, Line 44, in Claim 7, delete "independent" and insert -- independently --, therefor.

In Column 10, Line 45, in Claim 17, delete "radiofrequency" and insert -- radio frequency --, therefor.

Signed and Sealed this
First Day of October, 2024

Katherine Kelly Vidal
*Director of the United States Patent and Trademark Office*